United States Patent [19]

Kaschig

[11] Patent Number: 4,855,432
[45] Date of Patent: Aug. 8, 1989

[54] OPTICALLY ACTIVE IRIDIUM COMPLEXES AND THEIR USE

[75] Inventor: Jürgen Kaschig, Freiburg, Fed. Rep. of Germany

[73] Assignee: Ciba-Geigy Corporation, Ardsley, N.Y.

[21] Appl. No.: 47,098

[22] Filed: May 8, 1987

[30] Foreign Application Priority Data

May 16, 1986 [CH] Switzerland .................. 1987/86

[51] Int. Cl.$^4$ .................. C07B 41/02; C07F 15/00; B01J 31/22; C07D 213/53
[52] U.S. Cl. .................. 546/12; 502/155
[58] Field of Search .................. 546/12

[56] References Cited

PUBLICATIONS

Zussinovich, Journal of Organomet Chem., 222: pp. 323–329 (1981).
Brunner, Chem. Ber., 117: pp. 1330–1354 (1984).

*Primary Examiner*—Mark L. Berch
*Attorney, Agent, or Firm*—Harry Falber; Stephen O'Brien

[57] ABSTRACT

Optically active iridium complexes of the formula

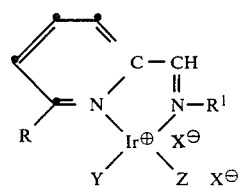

in which R is methyl and $R^1$ is a hydrocarbon radical having at least one chiral C atom or a hydrocarbon radical containing at least one hetero atom and having at least one chiral C atom; or R is a hydrogen atom and $R^1$ is 1,2-diphenylethyl or a 5-membered or 6-membered cycloaliphatic or cycloheteroaliphatic radical having at least two chiral C atoms and a phenyl group or alkyl group in the α-position, $X^\ominus$ is an anion of a monobasic inorganic or organic acid and Y and Z are each ethylene, or Y and Z together represent an open-chain or cyclic diene which has 6 to 10 C atoms and whose diene groups are bonded via 1 or 2 C atoms.

They are suitable as enantioselective, homogeneous catalysts for the transfer hydrogenation of, in particular, prochiral ketones with secondary alcohols.

8 Claims, No Drawings

OPTICALLY ACTIVE IRIDIUM COMPLEXES AND THEIR USE

The invention relates to optically active cationic iridium(I) complexes having asymmetric pyridinaldimine ligands and diene ligands, a process for their preparation and their use as enantioselective catalysts.

G. Zassinovich et al., in Journal of Organometallic Chemistry, 222, pages 323–329 (1981), describe cationic iridium(I) complexes having a 1,5-cyclooctadiene ligand and a 2-pyridinaldimine ligand which is substituted at the imine N atom by optically active α-phenylethyl or 3-pinanemethyl. They act as enantioselective homogeneous catalysts in the transfer hydrogenation of prochiral ketones with isopropanol. Although high yields are achieved in the reaction, the optical yield (enantiomeric excess) is relatively low.

It has now been found that the optical yield can be substantially increased if, in the stated iridium complexes, a methyl group is bonded at the 6-position in the pyridinaldimine ligand or a cyclic radical having at least two chiral C atoms and an alkyl or phenyl group in the α-position is bonded at the imine N atom of this ligand.

The invention relates to optically active iridium complexes of the formula (I)

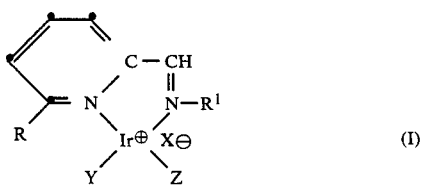

in which R is methyl and $R^1$ is a hydrocarbon radical having at least one chiral C atom or a hydrocarbon radical containing at least one hetero atom and having at least one chiral C atom; or R is a hydrogen atom and $R^1$ is 1,2-diphenylethyl or a 5-membered or 6-membered cycloaliphatic or cycloheteroaliphatic radical having at least two chiral C atoms and a phenyl group or alkyl group in the α-position, $X^-$ is an anion of a monobasic inorganic or organic acid and Y and Z are each ethylene, or Y and Z together represent an open-chain or cyclic diene which has 6 to 10 C atoms and whose diene groups are bonded via 1 or 2 C atoms.

Optically active means that at least one chiral C atom predominantly has the R or S configuration. The iridium complexes of the formula I also include mixtures of diastereoisomers.

$X^-$ as an anion of a monobasic inorganic or organic acid can be, for example, $F^\ominus$, $Cl^\ominus$, $Br^\ominus$, $J^\ominus$, $ClO_4^\ominus$, $NO_3^\ominus$, $BrO_3^\ominus$, $HSO_4^\ominus$, $H_2PO_3^\ominus$, $BF_4^\ominus$, $PF_6^\ominus$, $SbF_6^\ominus$, $A_sF_6^\ominus$, $SbCl_6^\ominus$, $SbCl_5F^\ominus$, $HCOO^\ominus$, $CH_3COO^\ominus$, $CCl_3COO^\ominus$, $CF_3COO^\ominus$, $CH_3SO_3^\ominus$, $CCl_3SO_3^\ominus$, $CF_3SO_3^\ominus$, phenyl-$SO_3^\ominus$ or p-toluyl-$SO_3^\ominus$. In a preferred embodiment, $X^\ominus$ is $BF_4^\ominus$, $ClO_4^\ominus$, $CF_3SO_3^\ominus$, $PF_6^\ominus$ or halide. Preferred halides are chloride, bromide and iodide.

Y and Z are each preferably ethylene, or Y and Z together are preferably a diene which has 6 to 8 C atoms and whose diene groups are bonded, in particular, via 2 C atoms. In a preferred embodiment, Y and Z are each ethylene, or Y and Z together are 1,5-cyclooctadiene, norbornadiene or 1,5-hexadiene.

A preferred subgroup of iridium complexes of the formula (I) comprises those in which R is methyl and $R^1$ is a radical of the formula II

in which $R^2$, $R^3$ and $R^4$ differ from one another if they do not contain at least 1 chiral C atom, and are a hydrogen atom, $C_1$–$C_4$-alkyl, $C_1$–$C_4$-alkoxy, cycloalkyl having 5 to 7 ring C atoms which is unsubstituted or substituted by $C_1$–$C_4$-alkyl or phenyl, cycloalkylalkyl which has 5 to 7 ring C atoms and 1 or 2 C atoms in the alkylene group and is unsubstituted or substituted by $C_1$–$C_4$-alkyl or phenyl, or are phenyl, naphthyl, benzyl or β-phenylethyl, or $R^3$ and $R^4$ together are $C_1$–$C_4$-alkyl-substituted or phenyl-substituted linear $C_4$- or $C_5$-alkylene, $C_3$- or $C_4$-oxaalkylene or $C_3$-dioxaalkylene having at least 1 chiral C atom.

The $C_1$–$C_4$-alkyl and $C_1$–$C_4$-alkoxy radicals can be methyl, ethyl, n-propyl, isopropyl, n-butyl, isobutyl, tert-butyl and their corresponding alkoxy radicals. Alkyl radicals $R^2$, $R^3$ and $R^4$ are preferably methyl or ethyl, and alkoxy radicals $R^2$, $R^3$ and $R^4$ are preferably methoxy. Cycloalkyl radicals $R^2$ to $R^4$ are preferably cyclopentyl, cycloheptyl and in particular cyclohexyl. Cycloalkylalkyl radicals $R^3$ and $R^4$ are preferably (cyclohexyl)methyl. $R^3$ and $R^4$ together as $C_3$- or $C_4$-oxaalkylene are preferably 2-oxapentylene, and as $C_3$-dioxaalkylene are preferably 2,4-dioxapentylene. $C_1$–$C_4$-alkyl as a substituent for $R^2$ to $R^4$ can be methyl, ethyl, n-propyl, isopropyl or butyl. Preferred substituents are methyl and phenyl.

$R^2$ in formula (II) is preferably H. A preferred subgroup comprising iridium complexes of the formula (I) in which $R^2$ is H, $R^3$ is $C_1$–$C_4$-alkyl, $C_1$–$C_4$-alkoxy or phenyl and $R^4$ is phenyl, benzyl or naphthyl, and $R^3$ and $R^4$ are not both phenyl; or $R^2$ and $R^4$ are each H, $R^3$ corresponds to the formula

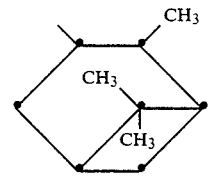

or the group $-CR^2R^3R^4$ corresponds to the formula

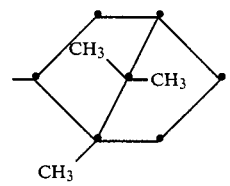

or $R^2$ is H and $R^3$ and $R^4$ are pentamethylene which is substituted in the 2-position by $C_1$–$C_4$-alkyl or 2,4-dioxapentylene which is substituted in the 1- and/or 3-position by $C_1$–$C_4$-alkyl or phenyl.

Another preferred embodiment comprises iridium complexes of the formula (I), in which R is a hydrogen atom and $R^1$ is 1,2-diphenylethyl or a radical of the formula

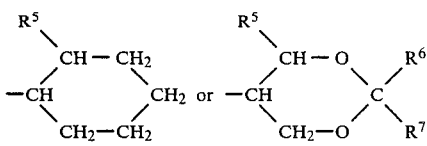

in which $R^5$ is $C_1$–$C_4$-alkyl, benzyl or phenyl and $R^6$ and $R^7$ independently of one another are H, $C_1$–$C_4$-alkyl or phenyl. $R^5$ is preferably phenyl or methyl and $R^6$ and $R^7$ are preferably H, methyl or phenyl. $R^5$ is particularly preferably phenyl and $R^6$ and $R^7$ are particularly preferably methyl, or $R^6$ is particularly preferably H and $R^7$ is particularly preferably phenyl.

The iridium complexes of the formula (I) can be obtained by processes which are known per se [see J. of Organom. Chem., 222, pages 323–329 (1981)], by reacting a diiridium complex of the formula [Ir(YZ)Cl]$_2$ with a pyridinaldimine of the formula (III)

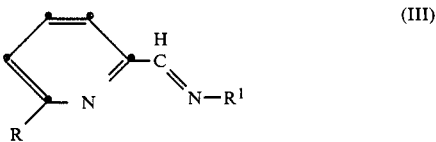

in which R, $R^1$, Y and Z have the abovementioned meaning, and then reacting the resulting chloride of the formula (I) with a salt $M^{\oplus}X'^{\ominus}$, in which M is an alkali metal and $X'^{\ominus}$ has the same meanings as $X^{\ominus}$—with the exception of chloride, in order to prepare other salts.

The diiridium complexes are known or can be prepared by known processes, by reacting a dichlorotetrakis(alkene)diiridium(I) (alkene: for example, cyclooctene) with ethylene or a diene YZ.

The reactions are carried out in general at temperatures of −10° to +30° C. in an inert solvent and in the absence of air. Examples of suitable inert solvents are hydrocarbons, such as benzene, toluene, xylene, petroleum ether, hexane, cyclohexane or methylcyclohexane; and ethers, such as, for example, diethyl ether, dibutyl ether, tetrahydrofuran and dioxane.

In the reaction, the chlorides of the formula (I) are initially obtained. To prepare the salts of the formula (I) having other anions of monobasic inorganic or organic acids, the chlorides of the formula (I) can be reacted, either directly after the reaction or after isolation and purification and redissolution in polar solvents (for example alcohols, ethers or ketones, with or without the addition of water), with an alkali metal salt $M^{\oplus}$, $X'^{\ominus}$, and then isolated. $X'^{\ominus}$ is an anion which differs from $X^{\ominus}$. $M^{\oplus}$ is preferably sodium. The iridium complexes according to the invention are crystalline and can be isolated by filtration and purified by recrystallization.

The pyridinaldimines of the formula (III) are known or can be obtained in a manner known per se, by reacting the unsubstituted or methyl-substituted 2-pyridinaldehyde with an amine $R^1NH_2$. Advantageously, pure stereoisomers of the amines $R^1NH_2$ are used, so that pure enantiomers of the formula (III) are obtained directly. However, it is also possible to use enantiomer mixtures and subsequently to resolve the resulting racemates of the formula (III) by well established methods.

Stereoisomers of the amines $R^1NH_2$ are known, and some of them are commercially available or can be prepared by known processes. Examples of such amines are: (R)-2-aminobutane, (R)-1-phenylethylamine, (S)-1-phenylethylamine, (R)-1-(α-naphthylethyl)-amine, (S)-2-amino-3-phenylpropane, (R)-1,2-diphenylethylamine, (S)-alaninol, (S)-phenylalaninol, (4S,5S)-5-amino-2,2-dimethyl-4-phenyl-1,3-dioxane, (S)-2-amino-1-methoxy-3-phenyl-propane, (R)-bornylamine, (R)-3-aminomethylpinane, (+)-dehydroabietylamine, (2R, 4S, 5S)-(+)-5-amino-2,4-diphenyl-1,3-dioxane [Chem. Ber. 113, pages 710–721 (1980)], (1S, 2R)-(−)-2-methylcyclohexylamine [Chem. Ber. 117, pages 2076–2098 (1984)] and (1S, 2S)-(+)-2-phenylcyclohexylamine [Chem. Ber. 117, pages 2076–2098 (1984)].

The invention furthermore relates to the use of the iridium complexes according to the invention as enantioselective homogeneous catalysts, in particular for the transfer hydrogenation of prochiral ketones with secondary alcohols. A particularly suitable secondary alcohol is isopropanol. The reaction is advantageously carried out in the absence of oxygen at elevated temperature. The secondary alcohol used is advantageously employed as the solvent. The amount of catalyst is preferably $10^{-2}$ to $10^{-5}$ mol/l, relative to the reaction volume. The reaction is preferably carried out in the presence of a base, in particular NaOH.

The Examples which follow illustrate the invention in more detail. The enantiomeric excess (ee) is determined according to Mosher [J. Org. Chem. 34, page 2543 (1969)].

EXAMPLES 1–10

0.2 g (0.226 mmol) of di-μ-chlorotetrakis(cyclooctene)diiridium(I) is dissolved in 18 ml of benzene under argon protective gas. In Examples 1, 3 and 5–10, 1.56 ml of 1,5-hexadiene are added at 10° C.; in Examples 2 and 4, ethylene is passed in at 5° C. in the course of 15 minutes.

After the mixture has been stirred for 30 minutes, 0.5 mmol of the 6-methylpyridine-2-aldehyde alkylimines (N,N ligand) substituted according to Table 1 is added. After the mixture has been stirred for 1 hour at room temperature, 40 ml of n-hexane are added under argon protective gas (in Examples 2 and 4, under an ethylene atmosphere). The desired product crystallizes out in the course of about 2 hours at 0° C.

In Examples 1, 3 and 5–10, the product is filtered off under suction under argon, washed with n-hexane and dried for about 16 hours under 0.1 Pa. In Examples 2 and 4, the product is filtered off under suction under ethylene gas, washed with n-hexane saturated with ethylene gas, and dried for 30 minutes at about 1 kPa.

The colour and the elemental composition of the complexes obtained are shown in Table 1.

TABLE 1

N,N is a pyridine-imine ligand of the form: pyridine ring with -CH₃ substituent and -A group, connected via =N-

| Example no. | Complex (HD = 1,5-Hexadiene) | A (absolute configuration) | Colour | Elemental analysis [% by weight] |
|---|---|---|---|---|
| 1 | [Ir(N,N)(HD)Cl] | −CH=N−CH(CH₃)−phenyl (S) | brick-red | Found: C 47.68; H 5.04; N 5.41; Cl 6.63<br>Calc.: C 47.22; H 4.91; N 5.25; Cl 6.64 |
| 2 | [Ir(N,N)(CH₂CH₂)₂Cl] | −CH=N−CH(CH₃)−phenyl (S) | brick-red | Found: C 44.99; H 4.50; N 5.42; Ir 36.90<br>Calc.: C 44.92; H 4.76; N 5.51; Ir 37.83 |
| 3 | [Ir(N,N)(HD)Cl] | −CH=N−CH−naphthyl (R) | brown | Found: C 53.15; H 4.96; N 4.59; Ir 31.50<br>Calc.: C 53.22; H 5.18; N 4.17; Ir 31.40 |
| 4 | [Ir(N,N)(CH₂CH₂)₂Cl] | −CH=N−CH(CH₃)−naphthyl (R) | bordeaux red | Found: C 50.41; H 4.92; N 4.87; Ir 33.90<br>Calc.: C 49.50; H 4.70; N 5.02; Ir 34.4 |
| 5 | [Ir(N,N)(HD)Cl] | −CH=N−CH(CH₃)−phenyl (S) | brick-red | Found: C 47.51; H 5.27; N 5.05; Cl 6.53<br>Calc.: C 48.21; H 5.15; N 5.11; Cl 6.47 |
| 6 | [Ir(N,N)(HD)Cl] | −CH=N−CH(OCH₃)−phenyl (S) | beige | Found: C 47.45; H 5.35; N 4.62; Ir 31.70<br>Calc.: C 47.78; H 5.23; N 4.85; Ir 33.25 |
| 7 | [Ir(N,N)(HD)Cl] | −CH=N−CH₂−pinanyl (1S, 2S, 3S, 5R) | pale red | Found: C 49.42; H 6.39; N 4.69; Ir 31.30<br>Calc.: C 49.68; H 6.25; N 4.83; Ir 33.13 |

TABLE 1-continued

N,N is

| Example no. | Complex (HD = 1,5-Hexadiene) | A(absolute configuration) | Colour | Elemental analysis [% by weight] |
|---|---|---|---|---|
| 8 | [Ir(N,N)(HD)Cl] | (1R) | brownish beige | Found:C 47.27; H 6.04; N 4.81; Calc.:C 48.79; H 6.05; N 4.95 |
| 9 | [Ir(N,N)(HD)Cl] | (2R, 4S, 5S) | pale brown | Found:C 52.29; H 4.87; N 3.90; Cl 5.25 Calc.:C 52.12; H 4.83; N 4.19; Cl 5.31 |
| 10 | [Ir(N,N)(HD)Cl] | (1S, 2R) | brick-red | Found:C 45.42; H 5.87; N 5,12; Cl 6,80 Calc.:C 45.66; H 5,75; N 5,32; Cl 6.74 |

EXAMPLE 11

214 mg (0.4 mmol) of the chloro complex obtained according to Example 1 is dissolved in a mixture of 32 ml of acetone and 8 ml of water under argon protective gas at 40° C. Two 150 mg portions of sodium iodide are added with a 30 minute interval at 25° C. A pale brown product crystallizes out at 0° C. It is filtered off under suction under argon, washed thoroughly with water and dried over phosphorus pentoxide for 20 hours under 1 Pa.
Yield: 120 mg
Elemental analysis:
Found: C 40.07; H 4.20; N 4.20; I 19.61; Ir 30.30%
Calculated: C 40.32; H 4.14; N 4.48; I 20.29; Ir 30.73%

EXAMPLE 12

534 mg (0.8 mmol) of the chloro complex obtained according to Example 9 are reacted with sodium iodide analogously to Example 11. 150 mg of dark olive green crystals are obtained.
Elemental analysis:
Found: C 45.20; H 4.32; N 3.45; I 16.26; Ir 25.30%
Calculated: C 45.85; H 4.25; N 3.69; I 16.70; Ir 25.30%

EXAMPLES 13-17

The substituted pyridine-2-aldehyde alkylimines (N,N ligand) described in Table 2 are reacted with di-μ-chlorotetrakis(cyclooctene)diiridium(I) and 1,5-hexadiene analogously to Examples 1-10. After working up in an analogous manner, the complexes listed in Table 2 are obtained.

EXAMPLE 18

523 mg (0.8 mmol) of the chloro complex obtained according to Example 13 are reacted with sodium iodide analogously to Example 11. 450 mg of a dark violet product are obtained.
Elemental analysis:
Found: C 44.66; H 4.34; N 3.34; I 16.84; Ir 25.20%
Calculated: C 45.10; H 4.06; N 3.76; I 17.02; Ir 25.78%

EXAMPLE 19

Preparation of

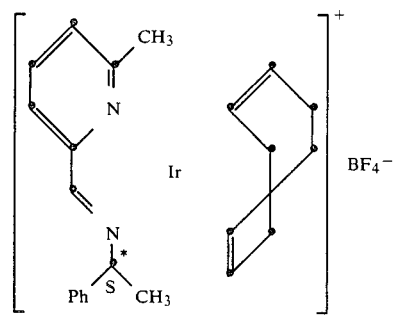

0.469 g (1.0 mmol) of bis-(acetonitrile)(cycloocta-1,5-diene)iridium tetrafluoborate is dissolved in 15 ml of dichloromethane under argon protective gas. A solution of 5 ml of dichloromethane and 1.0 mmol of 6-methylpyridine-2-[N-α-phenylethylaldimine] is added at room temperature. After 1 hour, the reaction mixture is evaporated to dryness under about 100 Pa. The oily mixture is washed several times with diethyl ether until it becomes solid. It is dissolved in 70 ml of methylene chloride, precipitated as a solid yellow precipitate with 100 ml of diethyl ether, filtered off and dried for 16 hours under 0.1 Pa.
Colour: yellow
Microanalysis ($C_{23}H_{28}N_2BFhd 4Ir$):

|  | C | H | N | F |
|---|---|---|---|---|
| Calculated: | 45.18 | 4.62 | 4.58 | 12.43 |
| Found: | 42.89 | 4.64 | 4.56 | 11.27 |

EXAMPLE 20 (USE EXAMPLE)

4.14 mg of a complex prepared according to Example 1 are dissolved in 36 ml of isopropanol in the absence of oxygen (argon atmosphere). After the mixture has been stirred for 1 hour at 60° C., 0.38 ml of 0.1N sodium hydroxide solution is added. Stirring is continued for a further hour at 60° C., and a solution of 36 ml of isopropanol and 1.43 g of butyrophenone is then added in the absence of oxygen. The molar ratio of substrate to catalyst is thus [s]/[cat.]=1000, and the catalyst concentration is $1.33.10^{-4}$ mol/l. After 21 hours at 60° C., the yield of 1-phenyl-1-butanol is determined as 69.7% by

TABLE 2

N,N is (pyridyl-imine structure with A substituent)

| Example no. | Complex (HD = 1,5-Hexadiene) | A (absolute configuration) | Colour | Elemental analysis [% by weight] |
|---|---|---|---|---|
| 13 | [Ir(N,N)(HD)Cl] | —CH=N— with phenyl-CH(O-CH(Ph)-O)- group (2R, 4S, 5S) | dark blue | Found: C 51.54; H 4.68; N 4.11; Cl 5.38<br>Calc.: C 51.41; H 4.62; N 4.28; Cl 5.42 |
| 14 | [Ir(N,N)(HD)Cl] | —CH=N— with phenyl-CH(O-C(CH$_3$)$_2$-O)- group (2R, 4S, 5S) | dark blue | Found: C 46.13; H 4.95; N 4.15; Ir 31.00<br>Calc.: C 47.55; H 4.99; N 4,62; Ir 31.71 |
| 15 | [Ir(N,N)(HD)Cl] | —CH=N— with cyclohexyl group (1S, 2S) | steel blue | Found: C 50.47; H 4.97; N 4.68<br>Calc.: C 50.20; H 5.27; N 4.88 |
| 16 | [Ir(N,N)(HD)Cl] | —CH=N— with CH$_3$-cyclohexyl group (1S, 2R) | violet | Found: C 44.31; H 5.60; N 5.49; Cl 6.86<br>Calc.: C 44.56; H 5.51; N 5.47; Cl 6.92 |
| 17 | [Ir(N,N)(HD)Cl] | —CH=N—CH with two phenyl groups (R) | dark blue | Found: C 50.17; H 4.79; N 4.53; Cl 6.01;[21]<br>Calc.: C 52.38; H 4.73; N 4.7; Cl 5.95; Ir 32.24 | weight by gas chromatography (OV 101, 120° C., isothermal).

To determine the enantiomer content according to Mosher, a sample of the reaction mixture (about 0.5 ml) is substantially freed from the solvent, and 50 ml of optically pure α-methoxy-α-trifluoromethylphenylacetyl chloride and 0.25 ml of dry pyridine are added at 0° C. After 15 minutes, the mixture is heated at 70° C. for 30 minutes and cooled, after which 3 ml of 10% citric acid solution are added and the diastereomeric esters are extracted with ether.

An enantiomer excess ee of (S)-1-phenyl-butanol of 49.2% is determined by gas chromatography (capillary column CW 20, 190° C.).

EXAMPLES 21 (USE EXAMPLE)

The complex according to Example 18 is used for the catalytic, enantioselective transfer hydrogenation of butyrophenone, analogously to Example 20.

After 25 hours, the yield of 1-phenyl-1-butanol is 68.6% by weight, and the enantiomer excess ee is 64.2% of (S).

I claim:

1. An optically active iridium complex of the formula (I)

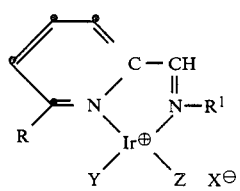

wherein R is methyl and $R^1$ is a radical of the formula II

in which $R^2$, $R^3$ and $R^4$ differ from one another if they do not contain at least 1 chiral C atom, and are a hydrogen atom, $C_1$-$C_4$-alkyl, $C_1$-$C_4$-alkoxy, cycloalkyl having 5 to 7 ring C atoms which is unsubstituted or substituted by $C_1$-$C_4$-alkyl or phenyl, cycloalkylalkyl which has 5 to 7 ring C atoms and 1 or 2 C atoms in the alkylene group and is unsubstituted or substituted by $C_1$-$C_4$-alkyl or phenyl, or are phenyl, naphthyl, benzyl or β-phenylethyl, or $R^3$ and $R^4$ together are $C_1$-$C_4$-alkyl-substituted or phenyl-substituted linear $C_4$- or $C_5$-alkylene, $C_4$- or $C_5$-oxaalkylene or $C_5$-dioxaalkylene having one, two, three or four chiral C atoms, or $R^2$ and $R^4$ are each H, and $R^3$ is

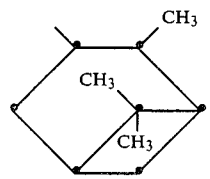

or the group —$CR^2R^3R^4$ corresponds to the formula

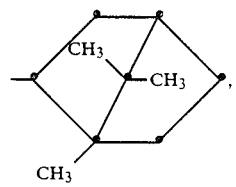

$X^\ominus$ is an anion of a monobasic inorganic or organic acid and Y and Z are each ethylene, or Y and Z together represent an open-chain or cyclic diene which has 6 to 10 C atoms and whose double bonds are separated by 1 or 2 carbon atoms.

2. An iridium complex of the formula (I) according to claim 1, wherein $X^\ominus$ is halide, $BF_4^\ominus$, $ClO_4^\ominus$, $CF_3SO_3^\ominus$ or $PF_6^\ominus$.

3. An iridium complex according to claim 2, wherein $X^\ominus$ is chloride, bromide or iodide.

4. An iridium complex of the formula (I) according to claim 1, wherein Y and Z are each ethylene, or Y and Z together are 1,5-cyclooctadiene, norbornadiene or 1,5-hexadiene.

5. An iridium complex of the formula I

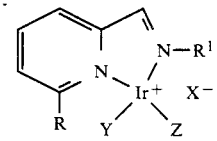

wherein R is H and $R^1$ is a radical of the formula

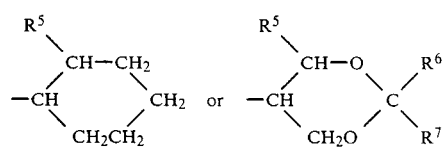

in which $R^5$ is $C_1$-$C_4$-alkyl, benzyl or phenyl and $R^6$ and $R^7$ independently of one another are H, $C_1$-$C_4$-alkyl, or phenyl, $X^-$ is an anion of a monobasic inorganic or organic acid and Y and Z are each ethylene, or Y and Z together represent an open-chain or cyclic diene which has 6 to 10 C atoms and whose double bonds are separated by 1 or 2 carbon atoms.

6. An iridium complex of the formula (I) according to claim 1, wherein $R^2$ is H.

7. An iridium complex of the formula (I) according to claim 5, wherein $R^5$ is phenyl and $R^6$ and $R^7$ are methyl, or $R^6$ is H and $R^7$ is phenyl.

8. An iridium complex of the formula (I) according to claim 1, wherein $R^2$ is H, $R^3$ is $C_1$-$C_4$-alkyl, $C_1$-$C_4$-alkoxy or phenyl and $R^4$ is phenyl, benzyl or naphthyl; or $R^2$ is H and $R^3$ and $R^4$ are pentamethylene which is substituted in the 2-position by $C_1$-$C_4$-alkyl or 2,4-dioxapentylene which is substituted in the 1- and/or 3-position by $C_1$-$C_4$-alkyl or phenyl.

* * * * *